US00PP22400P3

(12) United States Plant Patent
Benardella

(10) Patent No.: US PP22,400 P3
(45) Date of Patent: Dec. 27, 2011

(54) MINIFLORA ROSE PLANT NAMED 'BENSEIS'

(50) Latin Name: *Rosa hybrida*
Varietal Denomination: BENseis

(75) Inventor: Frank Benardella, Millstone Township, NJ (US); June E. Benardella, legal representative, Millstone Township, NJ (US)

(73) Assignee: Greenheart Farms, Inc., Arroyo Grande, CA (US)

( * ) Notice: Subject to any disclaimer, the term of this patent is extended or adjusted under 35 U.S.C. 154(b) by 0 days.

(21) Appl. No.: 12/802,068

(22) Filed: May 28, 2010

(65) Prior Publication Data

US 2011/0296567 P1 Dec. 1, 2011

(51) Int. Cl.
*A01H 5/00* (2006.01)

(52) U.S. Cl. ..... Plt./141

(58) Field of Classification Search ..... Plt./141, Plt./142, 143, 146, 147
See application file for complete search history.

*Primary Examiner* — Kent L Bell

(57) ABSTRACT

This new rose plant is of a medium size and upright growing habit. It bears hybrid tea-form flowers of great substance, primarily one to a stem. The flowers last very well on the plant making it an excellent decoration for the garden.

1 Drawing Sheet

Genus and species: *Rosa hybrida.*
Varietal denomination: 'BENseis'.

BACKGROUND OF THE INVENTION

The present invention relates to a new and distinct variety of hardy, bush-type rose plant of the miniflora class. This new variety is from a single seedling originated by Frank A. Benardella under controlled conditions in a greenhouse in Millstone Township (formerly Englishtown), N.J., by crossing the following two rose plants:

The seed parent is a miniflora rose, unnamed and unintroduced, developed in this same breeding program by crossing an unnamed and unintroduced 1994 seedling of this program by 'JACecond' (U.S. Plant Pat. No. 11,369).

The pollen parent is a miniature rose, unnamed and unintroduced, developed in this same breeding program, by crossing an unnamed and unintroduced 1990 seedling of this program by 'BENmagic' (U.S. Plant Pat. No. 8,603).

The primary goal of this breeding program was to produce unique, diminutive roses with award winning, hybrid tea form on plants having favorable attributes that will increase public appeal. To achieve this goal roses are selected for this hybridizing program primarily for their potentially award winning, hybrid tea form. Pertaining to this particular cross, both parents were seedlings noted to have hybrid tea form flowers.

SUMMARY OF THE INVENTION

The present invention relates to a new and distinct variety of vigorous, bush-type rose plant of the miniflora class. It is primarily characterized by vivid coral to red-orange flowers, having hybrid tea form, and borne on an upright bush growing two to three feet tall.

Though the new invention and its parents all have hybrid tea form flowers, they may be easily differentiated. This present plant has orange tones not noted in either parent.

The present plant may be compared with 'BENocho' (U.S. Plant Pat. No. 20,978) developed in this same breeding program and which is a direct descendant of 'JACecond', a grandparent of this new cultivar. Both cultivars have similar petal counts and those petals have similar form. Flowers of both are borne primarily singly on plants of upright habit. The most notable differences are the new invention has an orange tone in its flowers compared to the dark red and white bi-color flowers of 'BENocho', and the flowers of the current plant open slower and last considerably longer on the plant.

The field of comparison with other roses is greatly reduced by the unique coral color of its flowers. The new invention is further characterized by:

An abundance of flowers that are primarily borne singly;
Flowers that are slow to open;
Flowers lasting a month or longer on the plant;
Very slight to no fragrance;
An uniformly and well-branched plant;
Dark green, semi-glossy foliage;
Suitability for production from softwood cuttings in pots;
A plant that grows and blooms satisfactorily both in the greenhouse and outdoors and providing decoration in the garden as a perennial, in low borders or in large containers Asexual reproduction by cuttings of this new cultivar in Millstone Township, N.J., and Arroyo Grande, Calif., show that all distinguishing characteristics of this rose continually come true to form.

BRIEF DESCRIPTION OF THE DRAWING

The accompanying drawing consists of five separate numbered photographs depicting different parts of this current plant. Arranged counter clockwise from the top left corner of the page:

1) buds and flowers of this new cultivar as grown under plastic in Arroyo Grande, Calif. (about ⅔ scale)
2) a young plant as grown under lights with one opening bud (about ¼ scale)

3) profile view of an open bloom as grown in a greenhouse in Millstone Township, N.J. (about ⅔ scale)
4) a smaller scale image showing the coloring of the adaxial surfaces of the foliage
5) view of the branching habit showing stems, foliage and prickles of the current plant (about ½ scale)

Color is as nearly correct as is possible to make in color illustrations of this character.

BOTANICAL DESCRIPTION OF THE PLANT

The following observations, measurements, values and comparisons, in outline format, are from young plants (about 10 months old) of *Rosa hybrida*, 'BENseis'. These plants were initially grown in a plastic covered greenhouse in Arroyo Grande, Calif. for 7 to 9 months before they were shipped to Ipswich, Mass., where they were grown under florescent lighting. Upon arriving in Ipswich, they were fertilized with every watering with a 15-30-15 solution. All major color plate identifications made are referring to The Royal Horticulture Society Colour Chart except where common terms of color definition are employed. Phenotypic expression may vary with environmental, cultural and climatic conditions.

FLOWERS

Blooming habit: Primarily singly on strong stems; new shoots originate from nodes below the fading flower, allowing that cane to rebloom every 4 to 5 weeks; flowers remain fresh on the plant 4 weeks or more, allowing the mature plant to appear constantly in bloom Bud:
- *Form.*—Ovate with an obtuse base and acute apex.
- *Size.*—Diameter averaged ½ inch, varying from 15/32 to 17/32 inch. Length varied from 23/32 to 31/32 inch.

Sepals: Observed flowers had five sepals, permanently attached to the receptacle, opening ahead of the petals, reflexing to perpendicular to the receptacle; as the petals began to open, sepals continued to reflex to the peduncle
- *Form.*—Lanceolate; apices were acuminate and somewhat recurved, varying in intensity on each flower.
- *Surface texture.*—Outer surfaces: matte to semi-glossy and peppered with stipitate glands. Inner surfaces: Covered with a fine pubescence.
- *Color.*—Outer surface: dark yellow-green, between 146A and 146B; deeper green, between 131A and 137A, at and toward the apices and/or through the middle, wherever lighting was most intense; near 146C where lighting was less intense and where the sepals overlap; flushed with near 187A toward and at the apices and other areas where lighting was most intense. Inside surfaces: A light and muted yellow-green, between 195A and 147C.
- *Size.*—Extended beyond the tip of the bud by 31/32 inch before sepals divided; Widths varied from 9/32 to ½ inch. Lengths varied from 21/32 to 30/32 inch on newly opening flowers and 1 6/32 to 1 14/32 inch one week later. Inner sepals generally tended to be somewhat longer than outer sepals.
- *Margins.*—On outer sepals appeared glabrous with 1 to 3 foliar appendages along each margin, most often with 2. Inner sepals had no foliar appendages and finely pubescent margins.

Receptacle:
- *Form.*—Cuneate.
- *Size.*—11/32 inch tall as the flower first opens to 15/32 inch tall with full open bloom.
- *Diameter.*—7/32 to 11/32 inch at the top, tapered downward to 5/32 or 6/32 inch.
- *Surface/texture.*—Glabrous and glossy.
- *Color.*—Light yellow-green, between 145C and 142D.

Peduncle: Lengths varied from 1 1/16 to 2½ inches
- *Diameter.*—5/32 to 6/32 inch where it connected to the receptacle, tapering quickly to 4/32 or 5/32 inch, then tapering gradually to 3/32 inch where it connects to the stem.
- *Strength.*—Strong.
- *Surface.*—Glands and stipitate glands, vary from flower to flower in quantity from few to very many, and lengths vary from glands flat on the surface to stipitate glands up to ⅜ inch long.
- *Color.*—Between 146A and 138B, flushed with near 177A.

Blooms:
- *Form.*—High centered with a convex upper profile; the lower profile became flattened convex; minimal reflex of petals increased somewhat as flowers opened.
- *Size.*—Diameter of full open bloom varied from 3⅛ inches down to 2½ inches. Depths varied from 1⅜ inches to 1 inch, with 1 inch being the most common depth.
- *Petalage.*—The plants observed had 15 to 33 petals and 1 to 3 petaloids.
- *Lasting time on plant.*—Blooms were slow to open and lasted up to 4 weeks before beginning to fade; 6 to 7 weeks until all petals had dropped.
- *Fragrance.*—Very slight.

Petals: Imbricated.
- *Substance.*—Very good.
- *Thickness.*—Moderately thick.
- *Surfaces.*—Inside surfaces, velvety. Outer surfaces satiny, becoming leathery as the flower matured.
- *Appearance.*—Veins became increasingly raised somewhat on both surfaces as the flower matured.
- *Form.*—Outer petals, very broadly rounded. Inner petals, near oblate.
- *Margins.*—Rounded with an acute apex and a pronounced notch on either side of the apex.
- *Bases.*—Outer petals, obtuse. Inner petals, cuneate and often uneven, having one side somewhat longer than the other.
- *Color.*—Flowers appeared red as the blooms began to open and became coral as the flowers matured. When the sepals first divided, the color was a dark red, near 45A. During the first few days, adaxial surfaces were Vermillion Red, near 41A to a Scarlet Red, near 43A. Basal areas were near 2D. The two outermost petals had a pure white streak from the point of attachment, sometimes extending just beyond the basal area and sometimes extending upward for three-fourths of the petal, occasionally branching out a bit from one-fourth of the way up. The reverse of the petals was near 45C, suffused with between 51A and 53C from the center of the petals outward in all directions. Basal area was white, near 158D; point of attachment was a very pale yellow-green, near 146C. Veins in the basal area only were between 146B and 146C. Full-blown, adaxial surfaces of the outer petals were between 43A and 44B. Basal areas were white, near 155D, suffused with near 150D. Point of attachment was near 150D.

The reverse was near 52A and 50A towards the margins. Basal area was near 4D, with veins in the basal area near 146A. Point of attachment was near 145C. Differences on the intermediate and inner petals were the reverse being nearer 54A and having occasional streaks of near 149C. Adaxial surfaces of the inner petals were near 43C and near 52B along the margins. As blooms continued to age, petal surfaces became between 41B and 43B, areas along the margins became near 52C. Reverse of the inner petals became near 54A. At full fade adaxial surfaces were near 43C, suffused with near 66B.

Petaloids: Texture: same as petals

*Size.*—Up to ½ inch wide and up to ⅝ inch long.

*Color.*—Same as inner petals; often a pure white along one margin with a sterile anther attached to that margin.

*Unique characteristics.*—Sometimes attached by a long filament.

REPRODUCTIVE ORGANS

Stamens, filaments and anthers:

*Arrangement.*—Regularly arranged around styles.

*Quantity.*—125 to 130.

*Filaments.*—Length, 7/32 to 18/32 inch in full open flower, lengths varying greatly within each flower.

*General color.*—53B when young.

*Anthers.*—Egyptian Buff, near 19D.

*Pollen.*—Nasturtium Orange, near 25B.

Pistils, styles and stigmas:

*Quantity.*—About ½ to ⅔ as many as stamens.

*Styles.*—Thin and quite undulate. Length — 4/32 to 9/32 inch from the top of the receptacle. Color — Turkey Red, near 46C.

*Stigmas.*—Near 159A, from the Orange-White Group.

Hips: None observed

PLANT

Habit: Upright; well branched; flowers held well above plant

*Growth.*—Vigorous; uniform branching.

*Height.*—24 to 36 inches.

*Root initiation from cuttings.*—3 to 5 days in a controlled greenhouse environment.

Foliage: Pinnately compound, usually with 5 leaflets, but occasionally with 3 and rarely with 6 or 7 leaflets

*Size of mature leaf.*—4 to 5¼ inches.

*Leaflets.*—Shape — Ovate with an acute apex and oval base, with the exception that the base of the terminal leaflet tapered to the point of attachment. Size terminal leaflet — 2 to 2⅜ inches long and 1¼ to 1⅜ inches wide. Appearance — Upper surface semi-glossy; main vein recessed. Reverse, matte; main vein entirely protruding. Texture — Glabrous upper surface; leathery reverse. Serration — Simple. Color young foliage — Upper surface dark green near 136A, heavily flushed with deep Greyed-Purple near 187A. Reverse near 187B; main vein lighter, near 185A. Color mature foliage — Anthocyanin coloring, absent. Upper surface lightened somewhat and took on a bit of yellow tone, near 137A to between 137A and 139A. Reverse, dark yellow green near 147B.

Petiole/rachis/petiolules: Basal leaflets were often not attached directly opposite each other along the petiole/rachis. When the basal leaflets were not attached directly opposite, there was a difference of 3/32 inch from one side of the petiole to the other. The length of the petiole varied from 1 inch to 1 3/16 inch. Likewise, each side of the rachis could be a different length, varying between 28/32 and 1 1/32 inch on a five-leaflet leaf.

*Color on young foliage.*—The adaxial surface had a moderate flush of a medium Greyed-Purple, near 183A, and a medium yellow-green, and between the stipules near 146C. Reverse, medium Greyed-Purple, near 187D; near 146D between stipules.

*Color on mature foliage.*—Ridges of the adaxial surfaces of the petioles were dark green, between 137A and 137B; color in the groove, a light yellow-green near 145C. Abaxial surfaces were between 145C and 145B. Color along ridges of the rachis and petiolules was the same dark green as the leaflet surface, with near 138B in the groove, and near 145A on the abaxial surface.

Stipules: Length varied from 6/32 to 13/32 inch attached and 3/32 to 5/32 inch angled outward at about a 45° angle to the petiole. Stipules within a pair were not always the same length, varying by 1/32 inch.

*Margins.*—Somewhat sinuate; lined with stipitate glands.

*Edges.*—Usually lay flat.

*Color.*—A medium yellow-green near 146C on the adaxial surface on the mature leaf, near 145C along the petiole, and near 137A on the tips that were angled outward. Abaxial surface was near 145A.

Wood:

*Color of new growth.*—Medium green between 137C and 147B, heavily flushed with near 187A.

*Color old wood.*—Yellow-green, near 146A.

*Size.*—Main stems had a diameter of ¼ to 10/32 inch; Diameter primary laterals, 6/32 to 5/32 inch; Diameter secondary laterals, 5/32 inch. Flowering stems, diameter of 5/32 inch at the base, tapering to 3/32 inch, Length varied from 1 15/16 to 13½ inches, to the base of the peduncle.

*Texture.*—Main canes, coarse as a result of lenticels, otherwise glabrous. Primary laterals, glabrous. Secondary laterals were mostly glabrous, having a few prickles. Flowering stems were glabrous from the top downward; varying amounts of prickles formed from the base upward.

*Lenticels.*—Formed within the first year, near the base of the main canes and at the nodes with the primary laterals.

*Color.*—A grayed-brown, between 197A and 177D.

Prickles:

*Form.*—Upper profile, angled downward; lower profile, arcuate; the base was oval.

*Quantity.*—Main canes, no prickles. Primary laterals, an occasional single prickle. Secondary laterals, three to four prickles between each node, regardless of the distance between nodes. Flowering stems, heaviest near the base, with 3 to 8 between nodes; the upper portion of the flowering stems usually have no prickles.

*Size.*—5/32 inch long on primary laterals; about 11/32 inch long on secondary laterals; about 7/32 inch long on flowering stems.

*Color when young.*—Very dark red-purple, between 183B and 59B, becoming near 174C, a medium shade from the Greyed-Orange Group, at the tip.

*Color when old.*—Near 177C from the Greyed-Orange Group.

Resistance: Good resistance to blackspot and downy mildew; moderately susceptible to powdery mildew; no rust observed.

The invention claimed is:

1. A new and distinct variety of rose plant is claimed, substantially as described and illustrated herein.

* * * * *

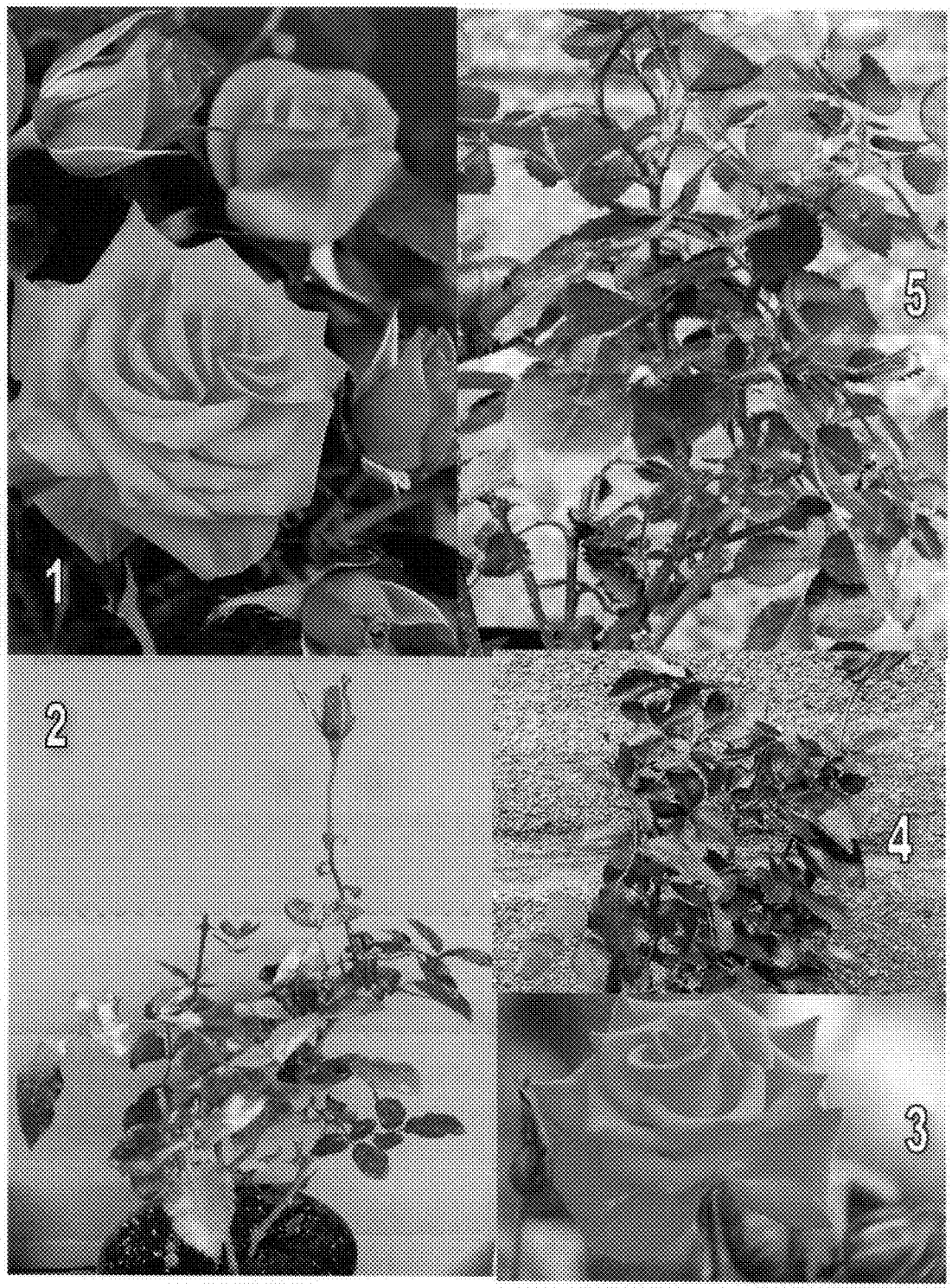
1
2
3
4
5